US006634884B2

(12) United States Patent  (10) Patent No.: US 6,634,884 B2
Phillips  (45) Date of Patent: Oct. 21, 2003

(54) FLUID ABSORBING BITE BLOCK

(76) Inventor: Yvonne M Phillips, P.O. Box 1525, Monroe, WA (US) 98272

( * ) Notice: Subject to any disclaimer, the term of this patent is extended or adjusted under 35 U.S.C. 154(b) by 132 days.

(21) Appl. No.: 09/904,340

(22) Filed: Jul. 11, 2001

(65) Prior Publication Data
US 2003/0039942 A1 Feb. 27, 2003

(51) Int. Cl.[7] .................................................. A61C 5/12
(52) U.S. Cl. ...................................... 433/138; 433/140
(58) Field of Search .......................... 433/140, 93, 136, 433/138

(56) References Cited

U.S. PATENT DOCUMENTS

| | | | | | |
|---|---|---|---|---|---|
| 1,973,615 | A | * | 9/1934 | Eustis | 433/140 |
| 2,614,325 | A | * | 10/1952 | Hartig | 433/138 |
| 2,651,109 | A | * | 9/1953 | Kanter | 433/136 |
| 2,930,128 | A | * | 3/1960 | Berens | 433/140 |
| 3,722,101 | A | * | 3/1973 | Via, Jr. | 433/140 |
| 4,372,314 | A | * | 2/1983 | Wall | 433/136 |
| 4,802,851 | A | * | 2/1989 | Rhoades | 433/140 |
| 5,199,872 | A | * | 4/1993 | Leal | 433/136 |
| 5,833,459 | A | * | 11/1998 | Graham | 433/138 |

* cited by examiner

Primary Examiner—Todd E. Manahan

(57) ABSTRACT

An absorbent core is contained within a generally wedge shaped shell. The core is constructed of cotton or other known absorbent material. The shell is constructed of a material which is rigid enough to hold a mouth of a patient in an open position when the bite block is inserted within the mouth, for example, foamed polystyrene. The shell has a first side and a second side, which are generally triangular shaped and opposite each other. The shell further includes a third side and a fourth side, which are generally rectangular, and which each span between the first and second sides of the shell. Each of the third and fourth sides include alternating peaks and valleys, for providing a gripping surface for the teeth of the patient. The first and second sides each contain an elongated side aperture therein. The core spans completely between the first and second sides at the side apertures. An end aperture is provided at the apex of the shell. The core spans completely to the end aperture.

3 Claims, 3 Drawing Sheets

FLUID ABSORBING BITE BLOCK

BACKGROUND OF THE INVENTION

1. Field of the Invention

The present invention relates to dental equipment for use in a patient's mouth during dental procedures, particularly to bite blocks and devices which absorb saliva

2. Description of the Related Art

In order to steady a patient's jaw, maintain the mouth of the patient in an open condition, and to improve access and visibility during dental procedures, devices known as bite blocks are positioned inside a patient's mouth. These devices do not absorb saliva, and so saliva must be routinely suctioned from around the bite block during the dental procedure.

Cotton rolls are often inserted into a patient's mouth between the cheek and gums and between the tongue and gums, to help absorb saliva. The problem is that these cotton rolls often become dislodged, interfering with the procedure, and triggering the gag reflex in the patient.

SUMMARY OF THE INVENTION

The saliva absorbing bite block of the present invention includes a generally wedge shaped shell and an absorbent core contained within the shell.

The core is constructed of cotton or other known absorbent material. The shell is constructed of a material which is rigid enough to hold a mouth of a patient in an open position when the bite block is inserted within the mouth.

The shell has a first side and a second side, which are generally triangular shaped and opposite each other. The shell further includes a third side and a fourth side, which are generally rectangular, and which each span between the first and second sides of the shell.

Each of the third and fourth sides include alternating peaks and valleys, for providing a gripping surface for the teeth of the patient. The first and second sides each contain an elongated side aperture therein. The core spans completely between the first and second sides at the side apertures. An end aperture is provided at the apex of the shell. The core spans completely to the end aperture. Because of the side and end apertures, saliva from a patient's mouth is absorbed into the bite block.

Still further features and advantages will become apparent from the ensuing description and drawings.

DETAILED DESCRIPTION

Figure 1:
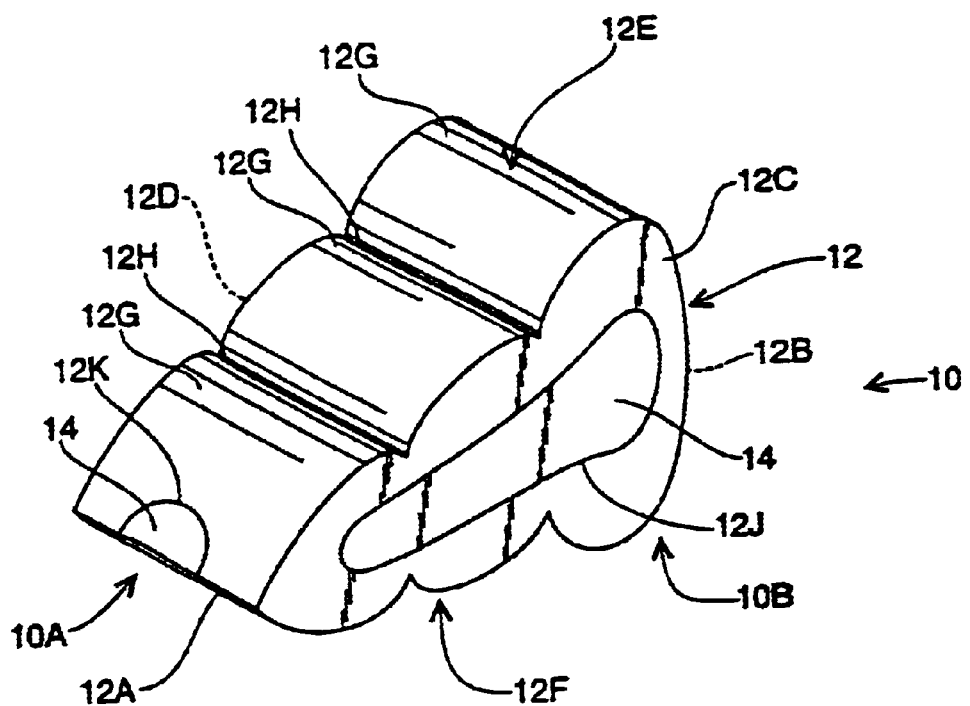
FIG. 1 is a perspective view of a first embodiment of a saliva absorbing bite block of the present invention.
Figure 2:
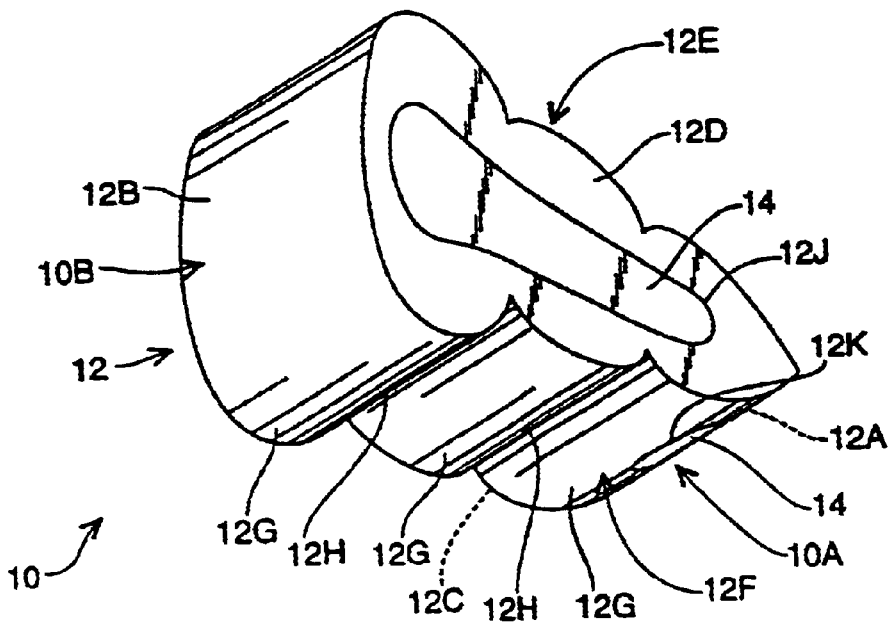
FIG. 2 is a perspective view of the first embodiment of the saliva absorbing bite block from a second viewpoint.
Figure 3:
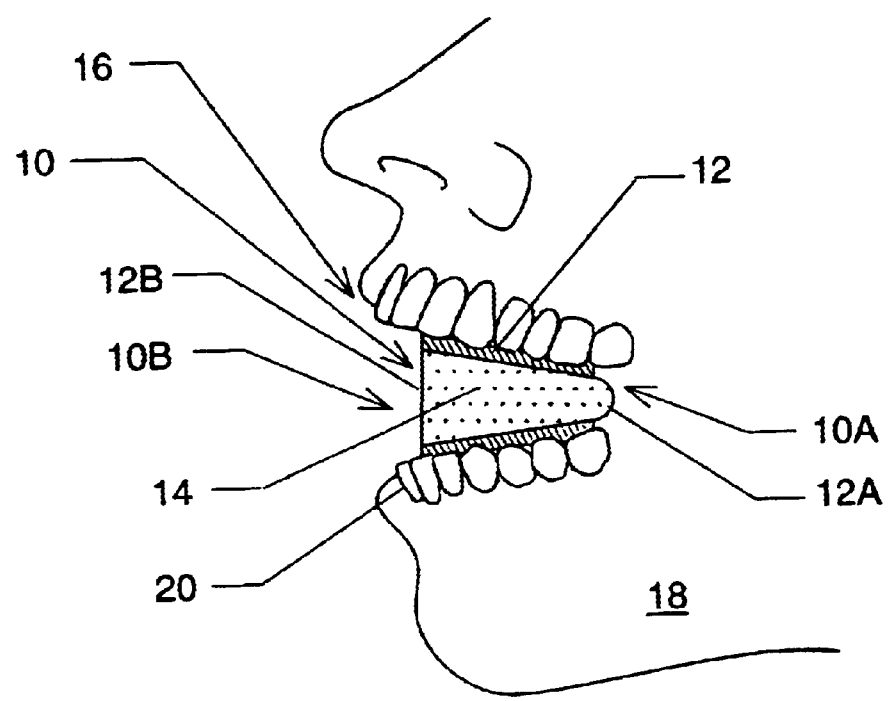
FIG. 3 is a sectional view of the first embodiment of the saliva absorbing bite block in use.

FIGS. 1 and 2 are perspective views of a first embodiment of a saliva absorbing bite block 10 of the present invention. FIG. 3 is a sectional view of the bite block 10 in use. Referring to FIGS. 1 and 2, the bite block 10 comprises a generally wedge shaped shell 12 having an apex 12A at a first end 10A of the bite block 10, and a base 12B at a second end 10B of the bite block 10.

Contained within the shell 12 is an absorbent core 14. The core 14 is constructed of cotton or other known absorbent material. The shell 12 is constructed of a material which is rigid enough to hold a mouth 16 of a patient 18 in an open position when the bite block 10 is inserted within the mouth 16. The material for the shell 12 may be foamed polystyrene, for example.

The shell 12 has a first side 12C and a second side 12D, which are generally triangular shaped and opposite each other. The shell 12 further includes a third side 12E and a fourth side 12F, which are generally rectangular, and which each span between the first and second sides 12A, 12B of the shell 12.

Each of the third and fourth sides 12E, 12F include alternating peaks 12G and valleys 12H, for providing a gripping surface for the teeth 20 of the patient 18.

The first and second sides 12C, 12D each contain an elongated side aperture 12J therein. The core 14 spans completely between the first and second sides 12C, 12D at the side apertures 12J. Saliva from the sides of the patient's mouth 16 is absorbed into the core 14 through the side apertures 12J.

An end aperture 12K is provided at the apex 12A of the shell 12. The core 14 spans completely to the end aperture 12K, permitting saliva from a rear of a patient's mouth 16 to be absorbed into the core 14 through the end aperture 12K.

As shown in FIG. 3, the bite block 10 is held between the teeth 20 of the patient 18 within the patient's mouth 16, with the wider, second end 10B disposed toward a front of the mouth 16, and a narrower, first end 10A disposed toward a rear of the mouth 16.

Figure 4:
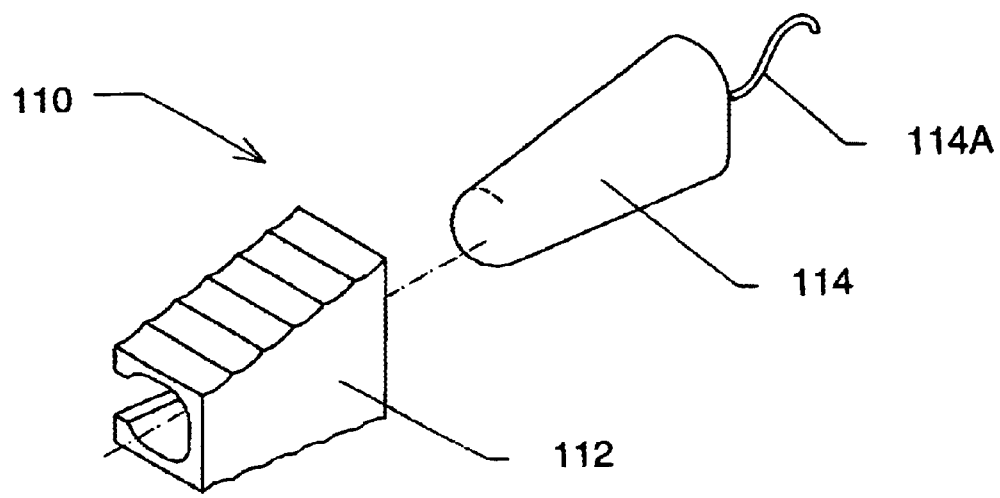
FIG. 4 is an exploded perspective view of a second embodiment of the saliva absorbing bite block.
Figure 5:
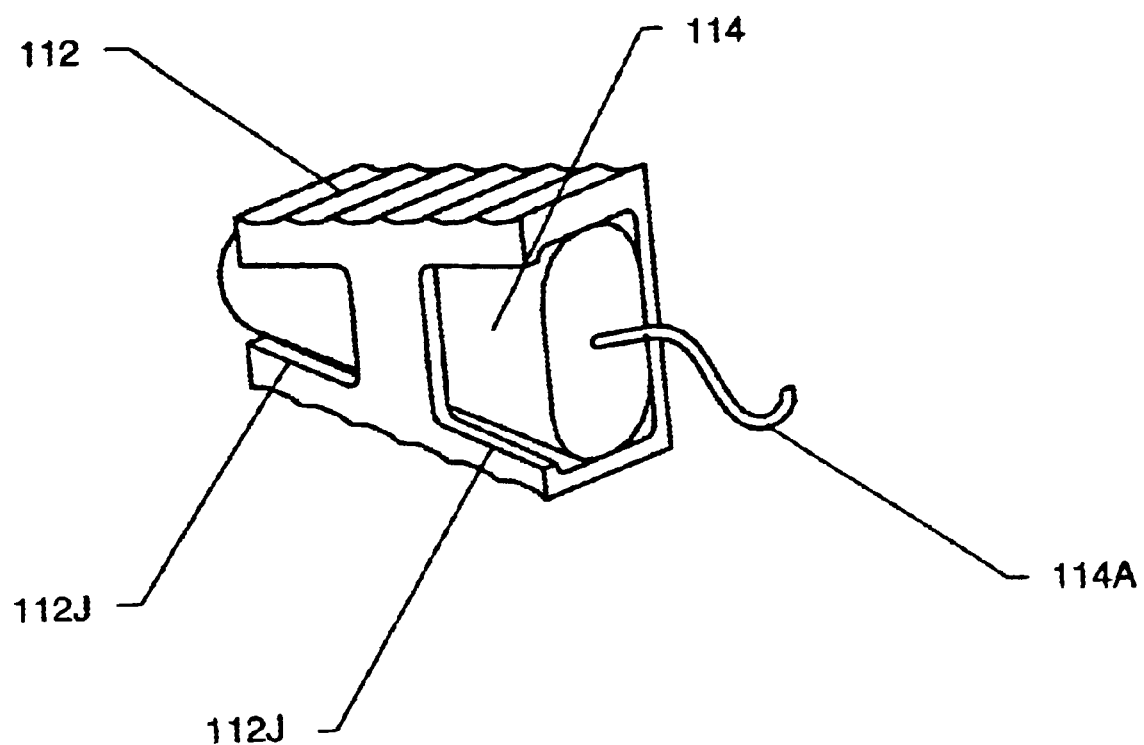
FIG. 5 is an assembled perspective view of the second embodiment of the saliva absorbing bite block, from a second viewpoint.

FIG. 4 is an exploded perspective view of a second embodiment of the saliva absorbing bite block 110. FIG. 5 is an assembled perspective view of the bite block 110, from a second viewpoint. In this particular embodiment, the bite block 110 comprises a wedge shaped shell 112 and a core 114. The shell 112 is autoclavable and reusable, being constructed for example of rubber coated steel. The core 114 includes a handle 114A, and is removable from the shell 112. Side apertures 112J within the shell 112 may be formed within one side of the shell 112 as shown, or may be formed on opposing sides thereof, similarly to the first embodiment of the bite block 10.

As shown, the second embodiment of the bite block 110 has the same general shape, function and features of the first embodiment of the bite block 10, except the core 114 is removable and the shell 112 is reusable and autoclavable.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. Accordingly, the scope of the invention is to be limited only by the following claims and their legal equivalents.

The invention claimed is:

1. A saliva absorbing bite block comprising:
   a) a generally wedge-shaped shell having upper and lower gripping surfaces and being rigid enough to hold the mouth of a patient open when inserted on either side of said mouth, directly between biting surfaces of maxillary and mandibular molars;

b) an absorbent core within said shell to absorb fluids from within the patient's mouth; and c) at least one aperture in the shell through which fluids are absorbed into the core.

2. A fluid absorbing bite block comprising:

a) a generally wedge shaped shell having a wide end and a narrow end, two generally triangular sides opposite each other and two generally rectangular sides each spanning between the generally triangular sides;

b) said shell to be rigid enough to hold the mouth of a patient open when the bite block is inserted in either side of the mouth directly between the biting surfaces of maxillary and mandibular molars;

c) an absorbent core within said shell to absorb fluids and saliva from within the patient's mouth;

d) a side aperture within at least one of the generally triangular sides through which said saliva can be absorbed into the said core;

e) a gripping means provided on each of the two generally rectangular sides; and f) an end aperture within the narrow end of the shell through which fluids from the patient's mouth can be absorbed into the core.

3. The saliva absorbing bite block of claim 2, wherein said shell is autoclavable and reusable, and said core is removable from the shell.

* * * * *